United States Patent
Al-Ali et al.

(10) Patent No.: US 8,385,995 B2
(45) Date of Patent: Feb. 26, 2013

(54) PHYSIOLOGICAL PARAMETER TRACKING SYSTEM

(75) Inventors: Ammar Al-Ali, Tustin, CA (US); Mohamed Diab, Mission Viejo, CA (US); Walter M. Weber, Laguna Hills, CA (US)

(73) Assignee: Masimo Corporation, Irvine, CA (US)

( * ) Notice: Subject to any disclaimer, the term of this patent is extended or adjusted under 35 U.S.C. 154(b) by 1604 days.

(21) Appl. No.: 11/834,602

(22) Filed: Aug. 6, 2007

(65) Prior Publication Data

US 2008/0027294 A1    Jan. 31, 2008

Related U.S. Application Data

(63) Continuation of application No. 10/930,048, filed on Aug. 30, 2004, now Pat. No. 7,254,431.

(60) Provisional application No. 60/498,749, filed on Aug. 28, 2003.

(51) Int. Cl.
*A61B 5/1455* (2006.01)

(52) U.S. Cl. .................... 600/310; 600/322; 600/323

(58) Field of Classification Search .................. 600/309, 600/310, 322, 323, 324, 326, 330, 331, 336, 600/301
See application file for complete search history.

(56) References Cited

U.S. PATENT DOCUMENTS

| | | | |
|---|---|---|---|
| 4,407,290 A * | 10/1983 | Wilber | .......................... 600/330 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |

(Continued)

*Primary Examiner* — Eric Winakur
*Assistant Examiner* — Chu Chuan (JJ) Liu
(74) *Attorney, Agent, or Firm* — Knobbe, Martens Olson & Bear LLP

(57) ABSTRACT

A physiological parameter tracking system has a reference parameter calculator configured to provide a reference parameter responsive to a physiological signal input. A physiological measurement output is a physiological parameter derived from the physiological signal input during a favorable condition and an estimate of the physiological parameter according to the reference parameter during an unfavorable condition.

5 Claims, 5 Drawing Sheets

U.S. PATENT DOCUMENTS

| | | | |
|---|---|---|---|
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,853,364 A * | 12/1998 | Baker et al. | 600/310 |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,990,426 B2 | 1/2006 | Yoon et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,186,966 B2 | 3/2007 | Al-Ali | |
| 7,190,261 B2 | 3/2007 | Al-Ali | |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali et al. | |
| 7,225,007 B2 | 5/2007 | Al-Ali | |
| RE39,672 E | 6/2007 | Shehada et al. | |
| 7,239,905 B2 | 7/2007 | Kiani-Azarbayjany et al. | |
| 7,245,953 B1 | 7/2007 | Parker | |

\* cited by examiner

PHYSIOLOGICAL PARAMETER TRACKING SYSTEM

CROSS-REFERENCE TO RELATED APPLICATIONS

This application is continuation of U.S. patent application Ser. No. 10/930,048 filed Aug. 30, 2004, which claims the benefit of U.S. Provisional Patent Application 60/498,749, titled "Physiological Parameter Tracking System" filed Aug. 28, 2003. The present application incorporates the above-cited patent application and provisional patent application herein by reference.

BACKGROUND OF THE INVENTION

Oxygen transport from the lungs to body tissue can be monitored by measuring various physiological parameters. For example, oxygen saturation of arterial blood ($S_aO_2$) is a measure of the ratio of oxyhemoglobin ($HbO_2$) concentration to the sum of $HbO_2$ and deoxyhemoglobin (Hb) concentrations in the arterial blood. Because $HbO_2$ is the major oxygen carrying component of blood, $S_aO_2$ is indicative of oxygen delivery to body tissues. As another example, oxygen saturation of venous blood ($S_vO_2$) is a similar measure of $HbO_2$ and Hb concentrations in venous blood and is indicative of oxygen consumption by body tissues. Measurements of the concentrations of carboxyhemoglobin (HbCO) and methemoglobin (MetHb) are indicative of abnormal hemoglobin constituents that interfere with oxygen transport.

Pulse oximetry is a noninvasive, easy to use, inexpensive procedure for measuring the oxygen saturation level of arterial blood. Pulse oximeters perform a spectral analysis of the pulsatile component of arterial blood in order to determine oxygen saturation ($S_{pa}O_2$), which is an estimate of $S_aO_2$. A pulse oximetry system has a sensor and a monitor. The sensor has emitters that typically consist of a red light emitting diode (LED) and an infrared LED that project light through blood vessels and capillaries underneath a tissue site, such as a fingernail bed. A sensor also has a detector that typically is a photodiode positioned opposite the LEDs so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

SUMMARY OF THE INVENTION

One aspect of a physiological parameter tracking system comprises a physiological signal and first, second, third and fourth calculators. The physiological signal has at least first and second intensity signal components received from a light-sensitive detector that detects light of at least first and second wavelengths transmitted through body tissue carrying pulsing blood. The first calculator is configured to output a reference parameter responsive to the physiological signal. The second calculator is configured to output an ancillary parameter responsive to the physiological signal. The third calculator is configured to output a slow parameter that is a function of the reference parameter and the ancillary parameter. The slow parameter is a function of time that is slowly varying relative to the reference parameter and the ancillary parameter. A fourth calculator is configured to output a physiological measurement responsive to the reference parameter and the slow parameter. In an embodiment, the fourth calculator provides a physiological measurement that is at least in part a function of the reference parameter and the slow parameter.

In an embodiment, the physiological measurement is a function of the reference parameter and the slow parameter during a first time interval and is the ancillary parameter during a second time interval. In an embodiment, the first time interval includes a period when calculations of the ancillary parameter are unfavorable. In an embodiment, the second time interval includes a period when calculations of the ancillary parameter are favorable.

Another aspect of a physiological parameter tracking system comprises inputting a physiological signal, deriving a physiological measurement from the physiological signal during a favorable condition, estimating the physiological measurement during an unfavorable condition and outputting a combination of the derived physiological measurement and the estimated physiological measurement. In an embodiment, estimating comprises calculating a slow parameter that is physiologically related to the reference parameter and the physiological measurement and tracking the reference parameter with the slow parameter. In an embodiment, outputting comprises selecting between estimated physiological measurement and derived measurement according to the favorable condition and the unfavorable condition. In an embodiment, the favorable condition and the unfavorable conditions relate to power consumption goals. In an embodiment, the favorable condition and the unfavorable conditions relate to the quality of the physiological signal.

A further aspect of a physiological parameter tracking system comprises a physiological signal input, a reference parameter calculator and a physiological measurement means for outputting and estimating. The physiological signal input has at least first and second intensity signal components received from a light-sensitive detector that detects light of at least first and second wavelengths transmitted through body tissue carrying pulsing blood. The reference parameter calculator is configured to output a reference parameter responsive to the physiological signal. The physiological measurement means outputs a physiological parameter derived from the physiological signal input during a favorable condition and estimates the physiological parameter according to the reference parameter during an unfavorable condition. In an embodiment, a slow parameter means relates the reference parameter to the physiological parameter during the unfavorable condition. In an embodiment, an update means selects a first time period for outputting the derived physiological parameter and a second time period for outputting the estimated physiological parameter.

DETAILED DESCRIPTION OF THE PREFERRED EMBODIMENTS

Overview

Figure 1:
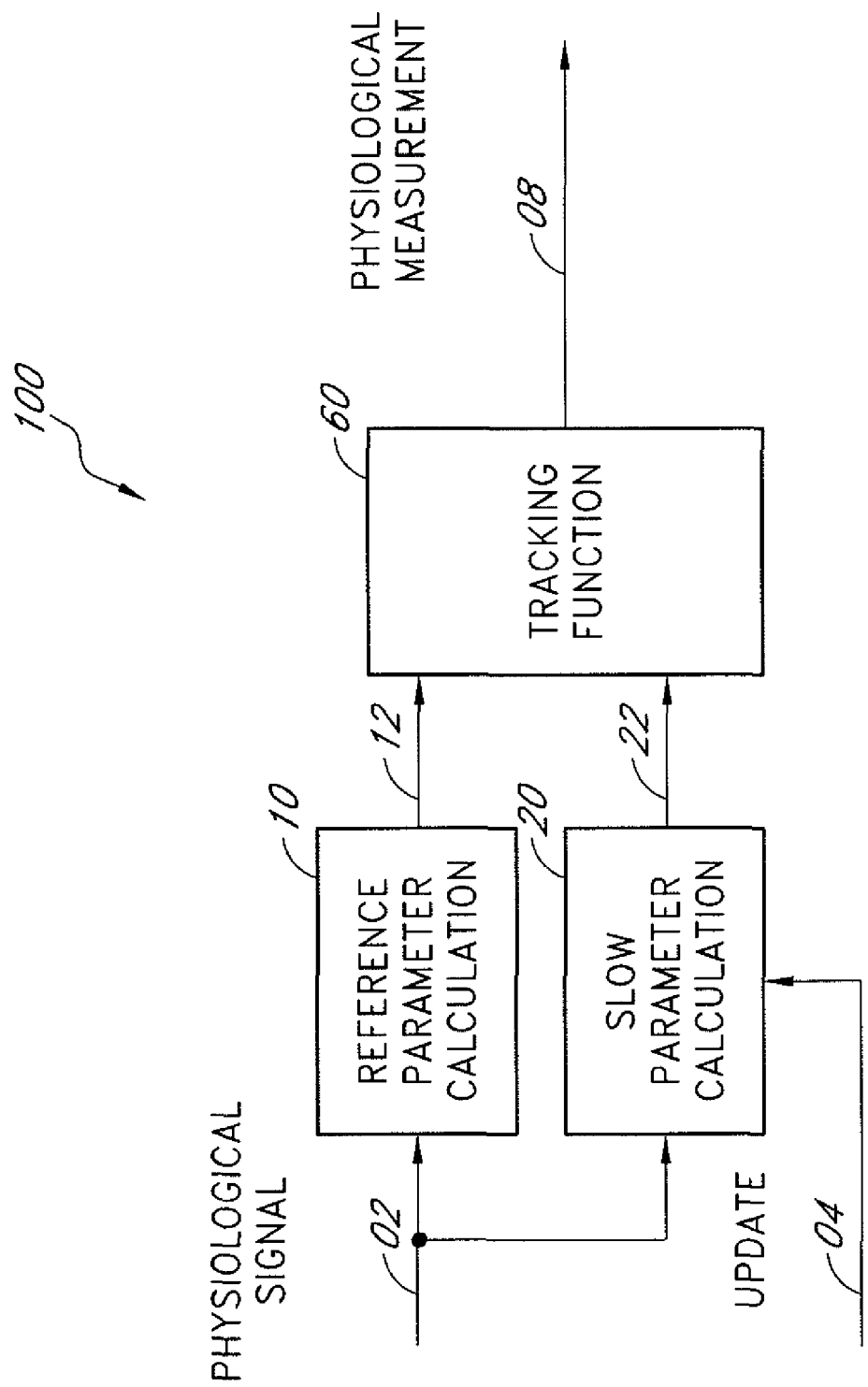
FIG. 1 is a block diagram of a slow parameter calculation embodiment of a physiological parameter tracking system.
Figure 4:
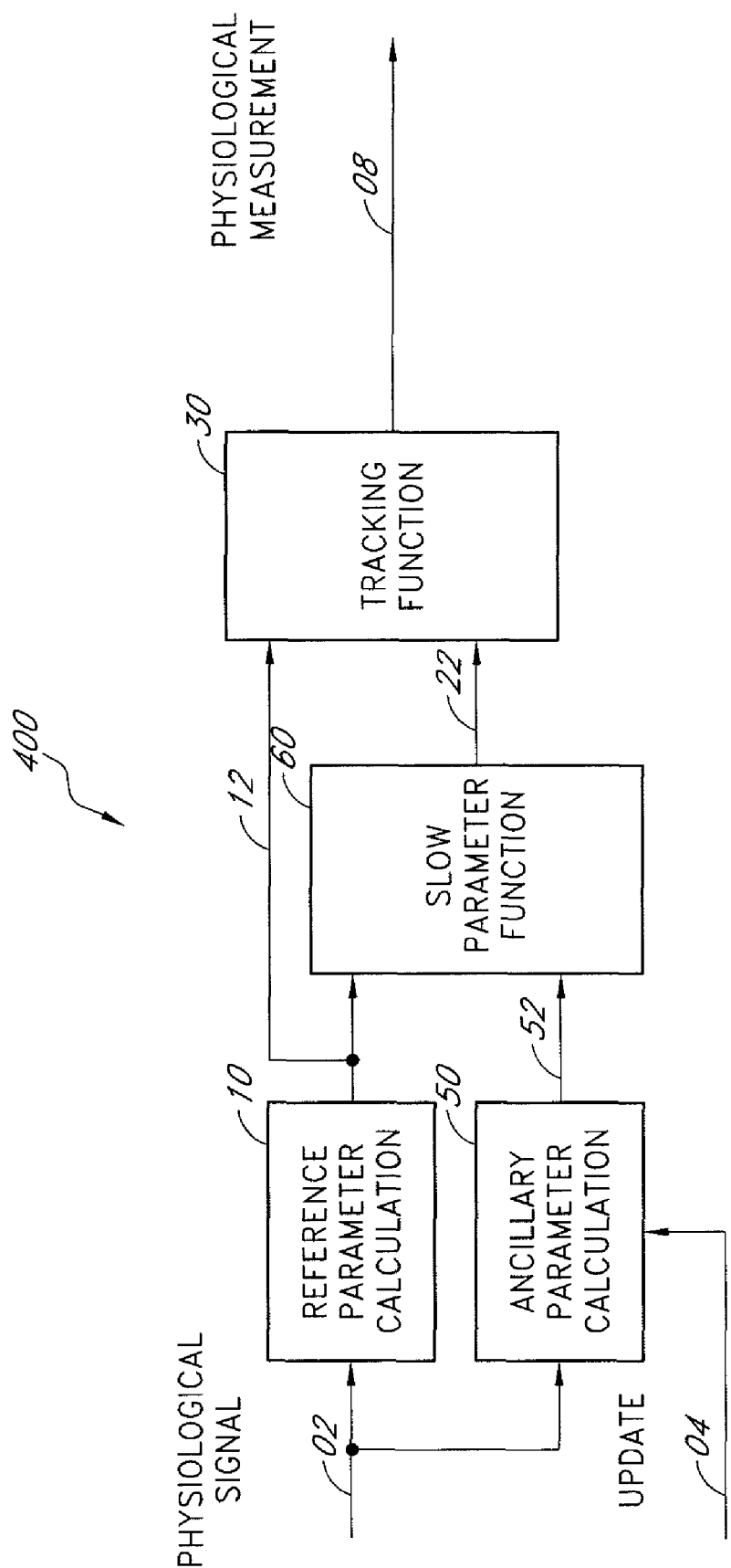
FIG. 4 is a block diagram of an ancillary calculation embodiment of a physiological parameter tracking system for operation in a S/H mode.
Figure 5:
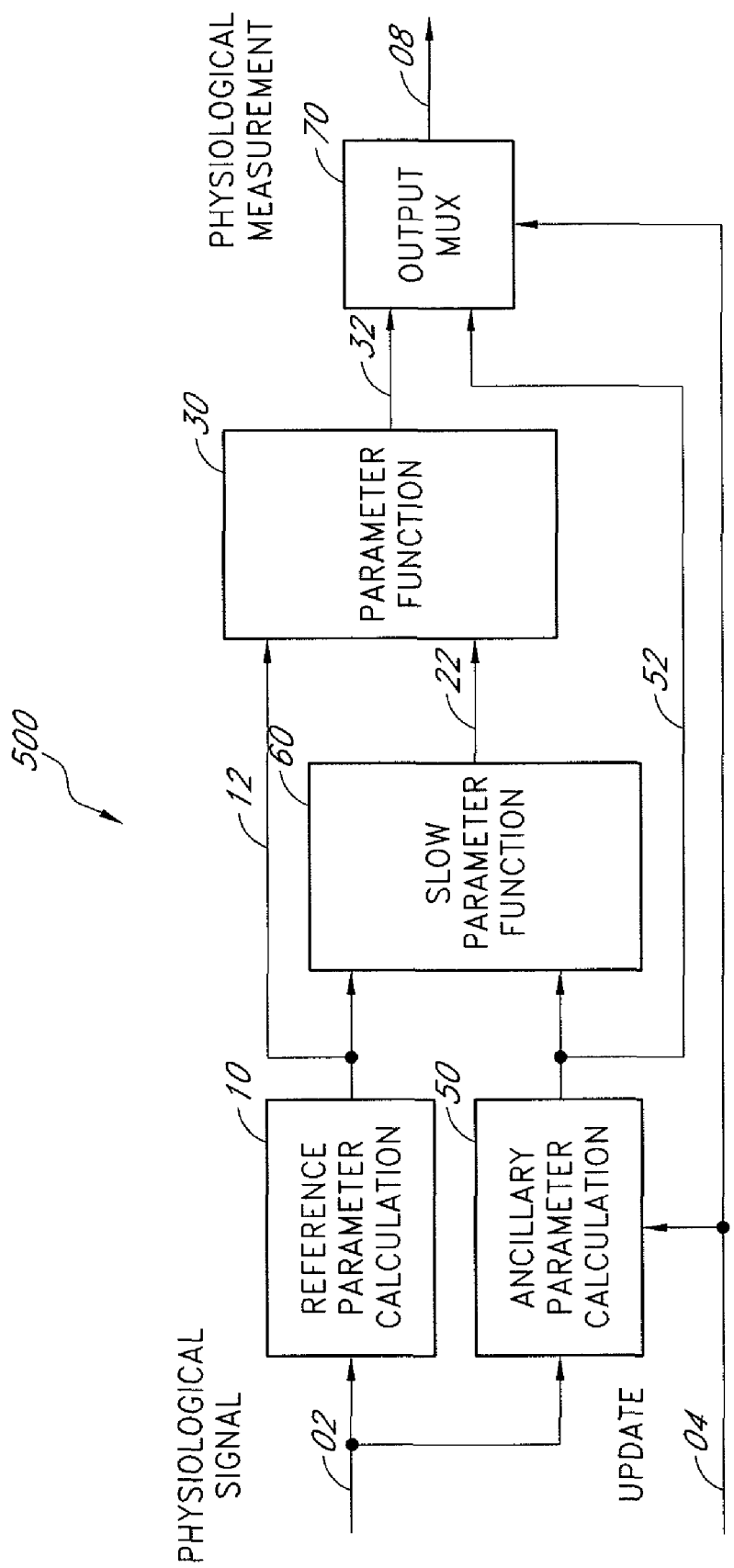
FIG. 5 is a block diagram of an ancillary calculation embodiment of a physiological parameter tracking system for operation in a T/H mode.

FIGS. 1, 4 and 5 illustrate embodiments of a physiological parameter tracking system that advantageously provide a clinically accurate physiological measurement by tracking a reference parameter based upon a slowly varying ("slow") parameter. As such, it is not necessary to continuously or frequently perform complex calculations to derive the physiological measurement. That is, the physiological measurement is a relatively simple function of the reference parameter and the slow parameter. Slow parameter calculations are performed only when conditions are favorable, or alternatively, suspended when conditions are not favorable, as indicated by an update command. The update command may be responsive to conditions such as power consumption goals or the quality of a physiological signal input to name a few.

In one embodiment, the slow parameter is HbCO or MetHb, and the reference parameter is $S_{pa}O_2$. Accordingly, the physiological measurement is $S_{pa}O_2$ corrected for the presence of one or both of these abnormal hemoglobin constituents. In another embodiment, the slow parameter is $\Delta_{av} = S_{pa}O_2 - S_vO_2$, a measure of oxygen consumption at a tissue site, and the reference parameter is $S_{pa}O_2$. Accordingly, the physiological measurement is an estimate of $S_vO_2$.

Slow Parameter Calculation

FIG. 1 illustrates a slow parameter calculation embodiment of a physiological parameter tracking system 100 in which the slow parameter 22 is derived from and responsive to a physiological signal 02. The physiological parameter tracking system 100 has a physiological signal 02 input, a reference parameter calculation 10, a slow parameter calculation 20 and a tracking function 30 and generates a physiological measurement 08 output. The reference parameter calculation 10 generates a reference parameter 12 from the physiological signal 02. The slow parameter calculation 20 generates the slow parameter 22 from the physiological signal 02 input. The tracking function 30 generates the physiological measurement 08 from the reference parameter 12 and the slow parameter 22.

As shown in FIG. 1, the physiological signal 02 is responsive to a physiological condition. In one embodiment, the physiological signal 02 originates from an optical sensor (not shown) attached to a tissue site. The sensor transmits multiple wavelengths of optical energy $\lambda_1, \lambda_2, \ldots, \lambda_n$ into the tissue site and detects corresponding optical energy emerging from the tissue site. The reference parameter calculation 10 may include pulse oximetry algorithms that operate on the physiological signal 02 to generate arterial oxygen saturation, $S_{pa}O_2$, as the reference parameter 12. A pulse oximetry signal processor and algorithms are described in U.S. Pat. No. 5,632,272 entitled Signal Processing Apparatus which is assigned to Masimo Corporation, Irvine, Calif. and incorporated by reference herein.

Also shown in FIG. 1, the slow parameter calculation 20 generates a slow parameter 22 from the physiological signal input 02 according to an update command 04. As an example, the slow parameter calculation 20 may include algorithms that operate on the physiological signal 02 to generate a measure of the concentration of abnormal hemoglobin, such as HbCO or MetHb. Multiple wavelength signal processing for measuring abnormal hemoglobin constituents, for example, is described in U.S. Provisional Patent App. No. 60/426,638 entitled "Parameter Compensated Physiological Monitor," U.S. Provisional Patent App. No. 60/428,419 entitled "Blood Parameter Measurement System," and U.S. Pat. No. 6,229,856 entitled Method and Apparatus for Demodulating Signals in a Pulse Oximetry System, which is assigned to Masimo Corporation, Irvine, Calif., all incorporated by reference herein.

Further shown in FIG. 1, the update command 04 may operate in a sample and hold (S/H) mode. That is, when the update command 04 is asserted, the slow parameter calculation 20 is triggered and the resulting slow parameter 22 value is held until a subsequent calculation. Operation of a physiological parameter tracking system having a S/H update is described with respect to FIG. 2, below. Alternatively, the update command 04 may operate in a track and hold (T/H) mode. That is, while the update command 04 is asserted, the slow parameter calculation 20 continues to generate values for the slow parameter 22. When the update command 04 is not asserted, the last generated value of the slow parameter 22 is held until the update command 04 is once more asserted. Operation of a physiological parameter tracking system having a T/H update is described with respect to FIG. 3, below.

TRACKING EXAMPLES

Figure 2:
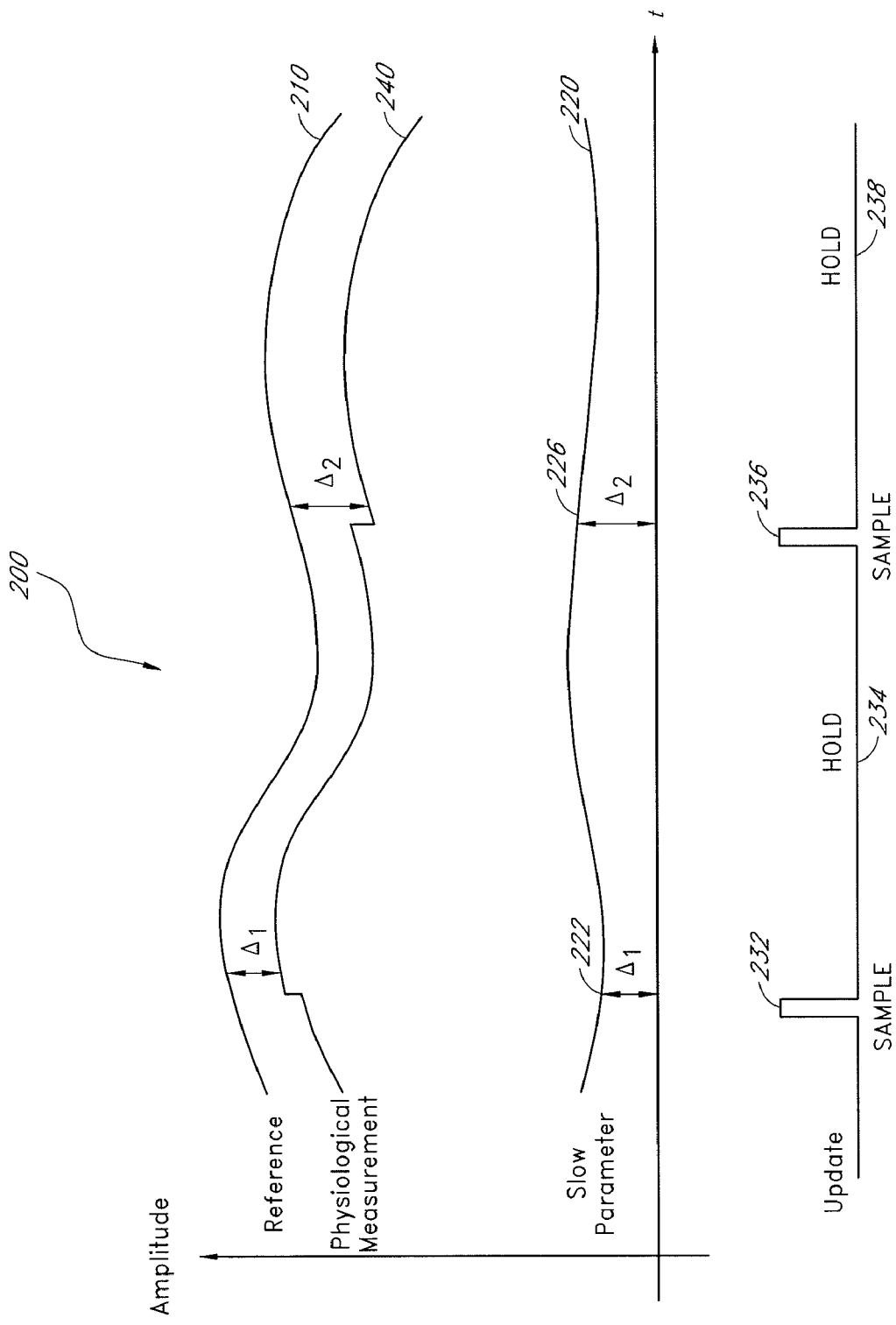
FIG. 2 is a graph illustrating operation of a physiological parameter tracking system in a sample and hold (S/H) mode.

FIG. 2 is an amplitude versus time graph 200 illustrating operation of a physiological parameter tracking system utilizing a S/H update. The graph 200 illustrates a reference curve 210 corresponding to a reference parameter 12 (FIG. 1) and a slow parameter curve 220 corresponding to a slow parameter 22 (FIG. 1). Below the graph 200 is a timing diagram 230 corresponding to the update command 04 (FIG. 1). A physiological measurement curve 240 corresponds to the physiological measurement 08 (FIG. 1).

As shown in FIG. 2, the physiological measurement curve 240 tracks the reference curve 210 according to a tracking function 30 (FIG. 1), which in this illustration is the difference between the reference parameter 12 (FIG. 1) and the slow parameter 22 (FIG. 1). A slow parameter 220 value is calculated at sample times 232, 236 and maintained throughout hold periods 234, 238. In particular, during a first sample time 232, a slow parameter value 222 of $\Delta_1$ is calculated, and during a second sample time 236, a slow parameter value 226 of $\Delta_2$ is calculated. As a result, during a first hold period 234, the physiological measurement curve 240 tracks the reference curve 210 by a difference of $\Delta_1$. Likewise, during a second hold period 238, the physiological measurement curve 240 tracks the reference curve 210 by a difference of $\Delta_2$. In this manner, the physiological measurement 240 is advantageously displayed with clinical accuracy utilizing only occasional computational resources and reducing power consumption accordingly.

Figure 3:
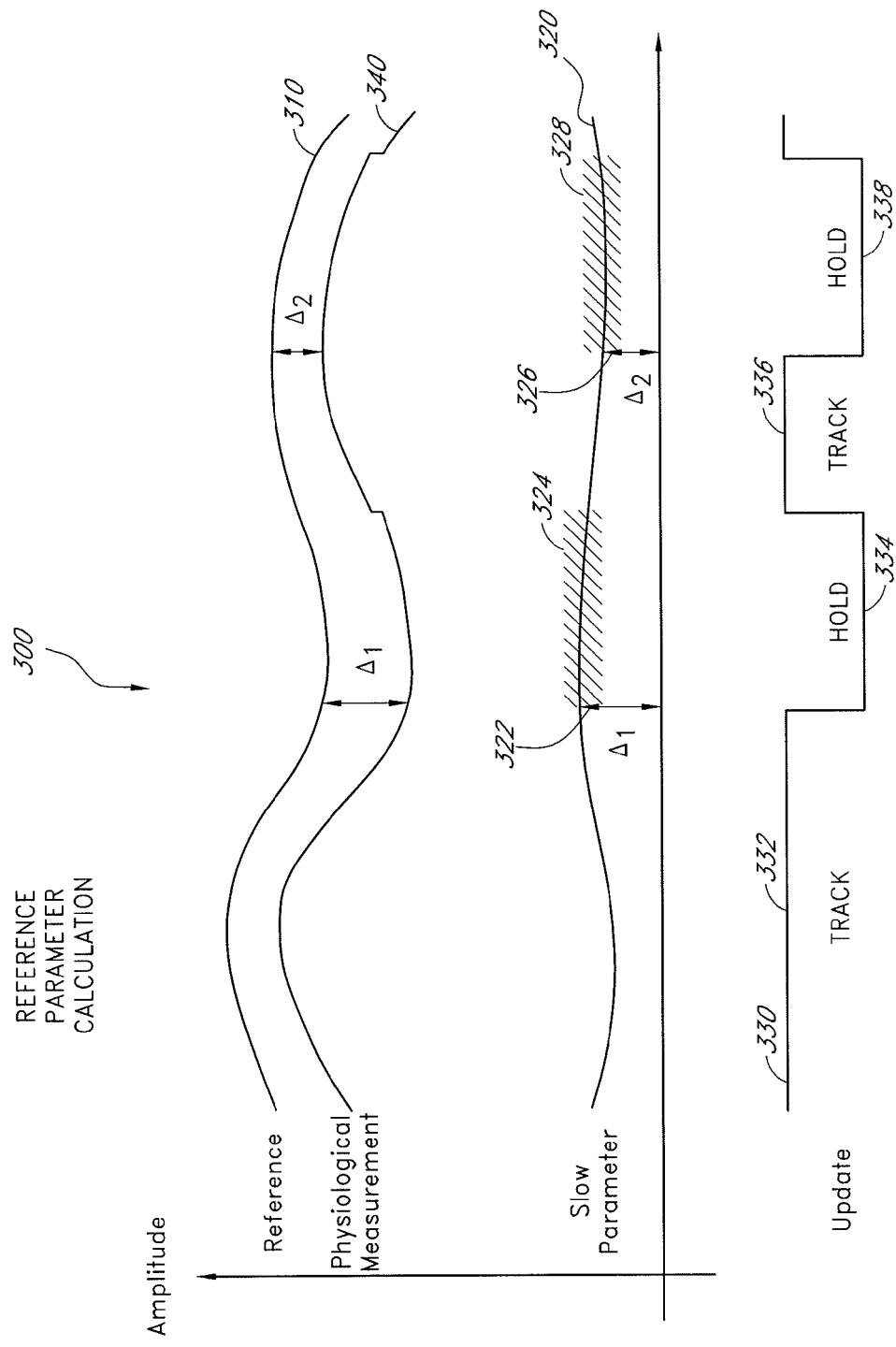
FIG. 3 is a graph illustrating operation of a physiological parameter tracking system in a track and hold (T/H) mode.

FIG. 3 is an amplitude versus time graph 300 illustrating operation of a physiological parameter tracking system utilizing a T/H update. The graph 300 illustrates a reference curve 310 corresponding to a reference parameter 12 (FIG. 1) and a slow parameter curve 320 corresponding to a slow parameter 22 (FIG. 1). Below the graph 300 is a timing diagram 330 corresponding to the update command 04 (FIG. 1). A physiological measurement curve 340 corresponds to the physiological measurement 08 (FIG. 1).

As shown in FIG. 3, the physiological measurement curve 340 tracks the reference curve 310 according to a tracking function 30 (FIG. 1), which, again, is the difference between the reference parameter 12 (FIG. 1) and the slow parameter 22 (FIG. 1). Slow parameter 320 values are calculated throughout track periods 332, 336, and the last computed values are maintained throughout the corresponding hold periods 334, 338. In particular, during a first track period 332, the physiological measurement curve 340 is the reference curve 310 minus the slow parameter curve 320. At the end of the first track period 332, a slow parameter value 332 of $\Delta_1$ is maintained throughout the first hold period 334. As a result, during the first hold period 334, the physiological measurement curve 340 is the reference curve 310 minus $\Delta_1$ and does not depend on the slow parameter curve 320. That is, during the first hold period 332, the physiological measurement curve 340 tracks the reference curve 310 by a difference of $\Delta_1$.

The "track" periods 332, 336 are so named because the slow parameter calculation 20 (FIG. 1) in response to the update timing 330 operates in a manner roughly analogous to a conventional track/hold amplifier when its output tracks the input. These are not to be confused with the periods when the physiological measurement curve 340 is "tracking" the reference parameter curve 310, which actually is during the hold periods 334, 338, when the slow parameter 22 (FIG. 1) output is held constant.

Also shown in FIG. 3, during a second track period 336, the physiological measurement curve 340 is again the reference curve 310 minus the slow parameter curve 320. At the end of the second track period 336, a slow parameter value 326 of $\Delta_2$ is maintained throughout the second hold period 338. As a result, during the second hold period 338, the physiological measurement curve 340 is the reference curve 310 minus $\Delta_2$ and does not depend on the slow parameter curve 320. That is, during the second hold period 338, the physiological measurement curve 340 tracks the reference curve 310 at a difference of $\Delta_2$.

Further shown in FIG. 3, the hold periods 334, 338 may correspond to slow parameter drop-out periods 324, 328, i.e. periods when the slow parameter cannot be accurately calculated. In this manner, the physiological measurement 340 is advantageously displayed with clinical accuracy even when noise or other signal corruption prevents measurement of the slow parameter 320.

Ancillary Parameter Calculation

FIG. 4 illustrates an ancillary parameter calculation embodiment of a physiological parameter tracking system 400 in which the slow parameter 22 is derived from an ancillary parameter 52 in S/H mode. The ancillary parameter 52, in turn, is derived from a physiological signal 02. That is, unlike the slow parameter calculation embodiment 100 (FIG. 1), the slow parameter 22 is only indirectly derived from and responsive to the physiological signal 02. The physiological parameter tracking system 400 has a physiological signal 02 input, a reference parameter calculation 10 and a tracking function 30, and, accordingly, generates a physiological measurement 08, similarly as described with respect to FIG. 1, above. However, in the ancillary calculation embodiment 400, the slow parameter 22 is a function 60 of the reference parameter 12 and/or an ancillary parameter 52. An ancillary parameter calculation 50 generates the ancillary parameter 52 from the physiological signal input 02 according to a S/H update command 04 input, such as described with respect to FIG. 2, above.

As an example, the ancillary parameter calculation 50 may include algorithms that operate on the physiological signal 02 to intermittently calculate venous oxygen saturation, $S_{pv}O_2$, as determined by a S/H update command 04. A corresponding slow parameter function 60 is the difference between an $S_{pa}O_2$ reference parameter 12 and the $S_{pv}O_2$ ancillary parameter 52 to yield a $\Delta_{av}$ slow parameter 22. Then, the tracking function 30 is a difference between the SpaO$_2$ reference parameter 12 and the sampled $\Delta_{av}$ slow parameter 22 to generate a $S_{pv}O_2'$ physiological measurement 08. That is, the physiological measurement 08 in this example advantageously provides a continuous measurement of venous saturation $S_{pv}O_2'$ utilizing intermittent calculations of $S_{pv}O_2$.

Apparatus and methods for determining $S_{pv}O_2$ from mechanical or ventilator induced perturbation of the venous blood volume are described in U.S. Pat. No. 5,638,816 entitled "Active Pulse Blood Constituent Monitoring" and U.S. Pat. No. 6,334,065 entitled "Stereo Pulse Oximeter," which are assigned to Masimo Corporation, Irvine, Calif. and are incorporated by reference herein.

FIG. 5 illustrates an ancillary parameter calculation embodiment of a physiological parameter tracking system 500 in which the slow parameter 22 is derived from an ancillary parameter 52 in T/H mode. The ancillary parameter 52, in turn, is derived from a physiological signal 02. The physiological parameter tracking system 500 has a physiological signal 02 input, a reference parameter calculation 10, an ancillary parameter calculation 50, a slow parameter function 60 and a tracking function 30, and, accordingly, generates a physiological measurement 08, similarly as described with respect to FIG. 4, above. However, in this ancillary calculation embodiment 500, the update command 04 operates in a track and hold mode, as described with respect to FIG. 3, above. Accordingly, the ancillary calculation embodiment 500 also has an output multiplexer 70 having the tracking function output 32 and the ancillary parameter 52 as inputs and the physiological measurement 08 as an output, as controlled by the update command 04 input. As such, the physiological measurement 08 is the ancillary parameter 52 during a track period 332, 336 (FIG. 3) of the update command 04 and is a function of the ancillary parameter 52 and the reference parameter 10 during a hold period 334, 338 (FIG. 3) of the update command 04. That is, the physiological measurement 08 is advantageously the ancillary parameter 52 except during a hold period, when the physiological measurement 08 tracks the reference parameter 12 according to the maintained value of the slow parameter 22.

As an example, the ancillary parameter calculation 50 may continuously calculate venous oxygen saturation, $S_{pv}O_2$, as determined by the update command 04 during track periods, and this calculation is provided as the physiological measurement 08. However, during hold periods of the update command 04, the physiological measurement 08 becomes $S_{pv}O_2'$, i.e. the $S_{pa}O_2$ reference parameter 12 minus a maintained value of the $\Delta_{av}$ slow parameter 22. The physiological measurement 08 in this example advantageously provides a measurement of venous saturation that is continuous through drop-out periods.

A physiological parameter tracking system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological parameter tracking system comprising:
   a physiological signal input having at least first and second intensity signal components received from a light-sensitive detector that detects light of at least first and second wavelengths transmitted through body tissue carrying pulsing blood;
   a first calculator configured to output a reference parameter responsive to the physiological signal;
   a second calculator configured to output an ancillary parameter responsive to the physiological signal;
   a third calculator configured to output a slow parameter that is a function of the reference parameter and the ancillary parameter and is slowly varying in time relative to the reference parameter and the ancillary parameter; and a fourth calculator configured to output a physiological measurement responsive to the reference parameter and the slow parameter, wherein the fourth calculator provides a physiological measurement that is at least in part of a function of the reference parameter and the slow parameter and wherein the physiological measurement is a function of the reference parameter and the slow parameter during a first time interval and is the ancillary parameter during a second time interval.

2. The physiological parameter tracking system according to claim 1 wherein the first time interval includes a period when calculations of the ancillary parameter are unfavorable.

3. The physiological parameter tracking system according to claim 2 wherein the second time interval includes a period when calculations of the ancillary parameter are favorable.

4. A physiological parameter tracking system comprising:

a physiological signal input having at least first and second intensity signal components received from a light-sensitive detector that detects light of at least first and second wavelengths transmitted through body tissue carrying pulsing blood;

a reference parameter calculator configured to output a reference parameter responsive to the physiological signal;

means for outputting a physiological parameter derived from the physiological signal input during a favorable condition and estimating the physiological parameter according to the reference parameter during an unfavorable condition;

means for relating the reference parameter to the physiological parameter during the unfavorable condition; and means for selecting a first time period for outputting the derived physiological parameter and a second time period for outputting the estimated physiological parameter.

5. A physiological parameter tracking system comprising:

a physiological signal input having at least first and second intensity signal components received from a light-sensitive detector that detects light of at least first and second wavelengths transmitted through body tissue carrying pulsing blood;

a reference parameter calculator configured to output a reference parameter responsive to the physiological signal;

a physiological measurement calculator configured to output a physiological parameter derived from the physiological signal input during a favorable condition and estimating the physiological parameter according to the reference parameter during an unfavorable condition;

a slow parameter calculator configured to relate the reference parameter to the physiological parameter during the unfavorable condition; and an update processor configured to select a first time period for outputting the derived physiological parameter and a second time period for outputting the estimated physiological parameter.

* * * * *